United States Patent [19]

Volk

[11] Patent Number: 5,436,680
[45] Date of Patent: Jul. 25, 1995

[54] INDIRECT OPHTHALMOSCOPY LENS PROVIDING APPARENT IMAGE CURVATURE

[76] Inventor: Donald A. Volk, 9378 Jackson, Mentor, Ohio 44060

[21] Appl. No.: 230,237

[22] Filed: Apr. 20, 1994

[51] Int. Cl.$^6$ .................................................. A61B 3/00
[52] U.S. Cl. .................................... 351/219; 351/205; 359/432
[58] Field of Search ............... 351/205, 216, 218, 219, 351/159, 160 R; 359/432

[56] References Cited

U.S. PATENT DOCUMENTS

| | | | |
|---|---|---|---|
| 4,728,183 | 3/1988 | Heacock et al. | 351/219 |
| 4,738,521 | 4/1988 | Volk | 351/205 |
| 5,007,729 | 4/1991 | Erickson et al. | 351/219 |
| 5,046,836 | 9/1991 | Volk | 351/219 |
| 5,189,450 | 2/1993 | Crossman et al. | 351/219 |
| 5,309,187 | 5/1994 | Crossman et al. | 351/219 |

Primary Examiner—William L. Sikes
Assistant Examiner—Huy Mai
Attorney, Agent, or Firm—Spencer, Frank & Schneider

[57] ABSTRACT

An ophthalmoscopy lens system is provided for collecting light rays emanating from a patient's eye and focussing the collected light rays to produce a real, aerial image of the fundus of the patient's eye. The ophthalmoscopy lens system includes a plurality of lens surfaces at least one of which is shaped to provide in conjunction with the other lens surfaces variable image distortion such that the aerial image, as viewed by an observer from a position anterior of the ophthalmoscopy lens system, has an apparent three dimensional concave curvature that imparts to the observer a sense of the actual concave curvature of the fundus being imaged.

21 Claims, 3 Drawing Sheets

INDIRECT OPHTHALMOSCOPY LENS PROVIDING APPARENT IMAGE CURVATURE

BACKGROUND OF THE INVENTION

The present invention relates an ophthalmoscopy lens system, and in particular to an indirect ophthalmoscopy lens system that collects light exiting a patient's eye and creates a real, aerial image of the fundus and vitreoretinal structures outside of a patient's eye for use in diagnostic and surgical procedures of the central and peripheral regions of the retina. Indirect ophthalmoscopy lens systems generally fall into two categories, namely non-contact and contact. The non-contact indirect ophthalmoscopy lens is generally a single lens which is either handheld by the observer or mounted by a device in front of a patient's eye for collecting light emerging from the patient's eye and forming a real, aerial image that can be either observed directly or photographed. The contact indirect ophthalmoscopy lens includes two or more lens elements mounted in a fixed relationship in a frame or holder, wherein one of the lens elements is a contact lens element adapted to be placed on the cornea of a patient's eye and the other lens or lenses operate to converge light emerging from the patient's eye and passing through the contact lens element to form a real, aerial image. Both types of lenses are generally used in the context of diagnostic and surgical procedures with a slit lamp biomicroscope, operating microscope, or other binocular instrument for binocularly and stereoscopically viewing the real image formed outside of the eye by the indirect ophthalmoscopy lens, as well as with still cameras and video recorders for monitoring and recording the observed real image.

In the past, indirect ophthalmoscopy lens systems were conventionally designed to produce a planar, aerial image of the retina, or at least an image that had a flat appearance, and which was additionally free of aberrations including field curvature and astigmatism. Lens designers of indirect ophthalmoscopy lens systems have in the past utilized various aspheric optical surfaces, including aspheric conoids and aspheric non-conoids, to correct the retinal image so that it appears to be generally flat and in clear focus with a minimum of optical aberrations. Such lens systems often incorporate aspheric curvatures on at least one surface of a possible multiplicity of lens elements to achieve the optical correction.

U.S. Pat. No. 5,046,836 discloses an indirect contact ophthalmoscopy lens system in which both the contact lens element and an anterior lens element incorporate aspheric contours on each lens element surface, for a total of four aspheric surfaces. Single, non-contact indirect ophthalmoscopy lenses are also known in which one or both surfaces of the lens have aspheric designs as disclosed for example in U.S. Pat. No. 4,738,521, the object always being to achieve a generally planar image corrected for optical aberrations.

U.S. Pat. No. 5,007,729 discloses a three element indirect contact ophthalmoscopy lens system wherein the lens of the preferred embodiment is stated to produce an image that is actually slightly concave in the anterior direction. As explained in that patent, if the optics were to produce a truly planar image, an optical illusion would result in which the image would appear to be slightly convex to the observer, that is the central portion of the image would appear to be closer to the observer than the peripheral region of the image. In order to correct for this non-planar appearance, U.S. Pat. No. 5,007,729 teaches designing the optics so that the peripheral portions of the aerial image are slightly closer to the observer than the central portion of the aerial image so that the image, although in actuality being slightly concave, has the appearance of being relatively flat.

In contrast to the known indirect ophthalmoscopy lens systems and the associated planar, aerial image, there are direct ophthalmoscopy lenses such as the Hruby lens, Goldmann fundus lens and the various plano-concave style vitreoretinal surgery lenses, which produce a virtual image of the retina that is narrow in extent of field and appears highly curved to a degree that it confirms to the practitioner the actual curvature of the retina. Physicians find this apparent retinal curvature desirable in that it preserves a realistic sense of the actual shape of the fundus oculi.

Although the desirability of a visualized image curvature corresponding to the actual curvature of the retina obtained with the use of direct ophthalmoscopy lenses has long been appreciated, until now, this feature has not been achieved in indirect ophthalmoscopy to create an image of similar apparent curvature. One reason for this may be that to introduce a true curvature to the real image formed by an indirect ophthalmoscopy lens would cause those portions of the curved image not directly viewed to be out of focus to the observer. This would require the observer to continually readjust the focus of the slit lamp biomicroscope in order to maintain clear retinal imagery when viewing different portions of the aerial image. Even the slight curvature of the image as disclosed by U.S. Pat. No. 5,007,729, which is intended to provide the appearance of a relatively flat field, will require adjustment of the slit lamp microscope in order to maintain clarity and focus when viewing portions of the fundus image having different focal positions.

While flattening of the aerial image produced by an indirect ophthalmoscopy lens is necessary to maintain a clear and consistent focus over the entire fundus image, this flatness has its disadvantages. As mentioned above, the planar image does not present a realistic curvature of the visualized retina as compared to that of the virtual image produced by the direct ophthalmoscopy lens. Additionally, the same optical quality which imparts flatness to the image also causes instrumentation inserted into the eye, for example during vitreoretinal surgery, to attain a distorted curvature, potentially leading to misinterpretation of the location of the instrument and the region of the retina being viewed.

SUMMARY OF THE INVENTION

It is an object of the present invention to provide an improved indirect ophthalmoscopy lens system that is substantially corrected for optical aberrations including field curvature, astigmatism and coma, while simultaneously providing an apparent concave curvature to the real, aerial image of the retina.

It is another object of the invention to provide an indirect ophthalmoscopy lens system of the above type that employs one or more lens elements.

It is another object of the invention to provide an indirect ophthalmoscopy lens system of the above type that is constructed as a non-contact lens.

It is another object of the invention to provide an indirect ophthalmoscopy lens system of the above type that is constructed as a contact lens.

It is another object of the invention to provide an indirect ophthalmoscopy lens system of the above type for use with an operating microscope in conjunction with vitreoretinal examination, treatment, or surgery.

It is another object of the invention to provide an indirect ophthalmoscopy lens system of the above type with particular distortion characteristics that impart to the practitioner a sense of the actual curvature of the retina being imaged by the ophthalmoscopy lens.

It is another object of the invention to provide an indirect ophthalmoscopy lens system of the above type that provides an aerial image with continuously and progressively variable magnification across its extent to simulate the three-dimensional nature of the actual retina.

The above and other objects are accomplished in accordance with the invention by the provision of an ophthalmoscopy lens system for collecting light rays emanating from a patient's eye and focussing the collected light rays to produce a real aerial image of the fundus of the patient's eye that is corrected for optical aberrations, and wherein the ophthalmoscopy lens system further includes a plurality of lens surfaces which collectively provide a variable distortion over the extent of the real aerial image so that the aerial image, as viewed by an observer from a position anterior of the ophthalmoscopy lens system, has an apparent three dimensional concave curvature.

Variable distortion is conventionally described herein as a percentage of distortion over a normalized field of view and has a direct correspondence to relative magnification of the image over the same field of view. An increasing distortion over a portion of the field of view corresponds to an increasing magnification and, likewise, a decreasing distortion over a portion of the field of view corresponds to a decreasing magnification. Thus, as used herein, variable distortion could be interchangeably used with variable magnification.

In accordance with the invention, one or more aspheric, non-conoidal surfaces are employed which, interacting together and with any other lens elements utilized in the system, provide the variable distortion (magnification). The character of the variable distortion must be continuous and progressive, increasing the retinal image size peripheralward in the central region of the aerial image and reducing the lateral magnification and compressing the image in a peripheral region of the image. Such an optical character with its specific retinal image sizing provides a sense of the three dimensional contour of the globe when the retinal image is viewed binocularly and stereoscopically. The principles of the invention are equally applicable to contact and non-contact indirect ophthalmoscopy lens systems.

In order to provide the specified variable distortion, a complex lens surface of variable curvature is employed on at least one of the elements of the imaging system. Such a curvature may be mathematically defined according to apical radius, apical eccentricity and additional higher order terms or conic deformation values by the following conventional polynomial expression:

$$Y = (2rx + (e^2 - 1)x^2)^{\frac{1}{2}} + Ax^F + Bx^G + Cx^H$$

where Y is the semi-diameter distance from the optical axis; r is the apical radius of curvature; e is the apical eccentricity; x is the distance from the apex of the surface along its axis of revolution; A, B and C are constant coefficients; and F, G and H are constant exponents.

The higher order aspheric terms $Ax^F$, $Bx^G$, $Cx^H$ are used to achieve the continuous and progressive change in retinal image size characterizing the aerial image of the present invention. Due to their complexity, higher order aspheric surfaces are often, out of convenience, compared to the simpler and more easily understood conoid with its approximate, though different profile. An analysis of the higher order aspheric surface design using a so-called "best fit conic" approach would necessarily be in error, however, as the defined polynomial aspheric curvature employed in the present invention, defines a non-conoidal curvature substantially different in profile and more significantly different in function from that of a pure conoid, as those skilled in the art will appreciate from the ensuing specification.

Through experimentation and testing it has been found that the appropriate aspheric surface is one with an apical eccentricity substantially increased over that required to produce a flat appearing image, one with progressively decreasing eccentricity from apex to periphery, and peripheral eccentricity values substantially lower than corresponding peripheral eccentricity values for a lens producing a flat appearing retinal image.

The balance of high apical eccentricity and progressively decreasing and reduced eccentricity peripheralward should average to provide generally well corrected sagittal and tangential fields, along with the desired variable distortion.

DETAILED DESCRIPTION OF THE INVENTION

The invention will now be described in detail by way of two specific examples which are in no way intended to be limiting of the invention as hereinafter claimed. The principles of the present invention apply equally well to indirect ophthalmoscopy lenses of the contact and non-contact type and as utilized with an indirect ophthalmoscope, slit lamp biomicroscope, operating microscope, or other instrument, as well as for use in photographic and video monitoring and recording applications. As such, a variety of lenses of different design, power and configuration may be utilized within the scope of the invention.

Figure 1:
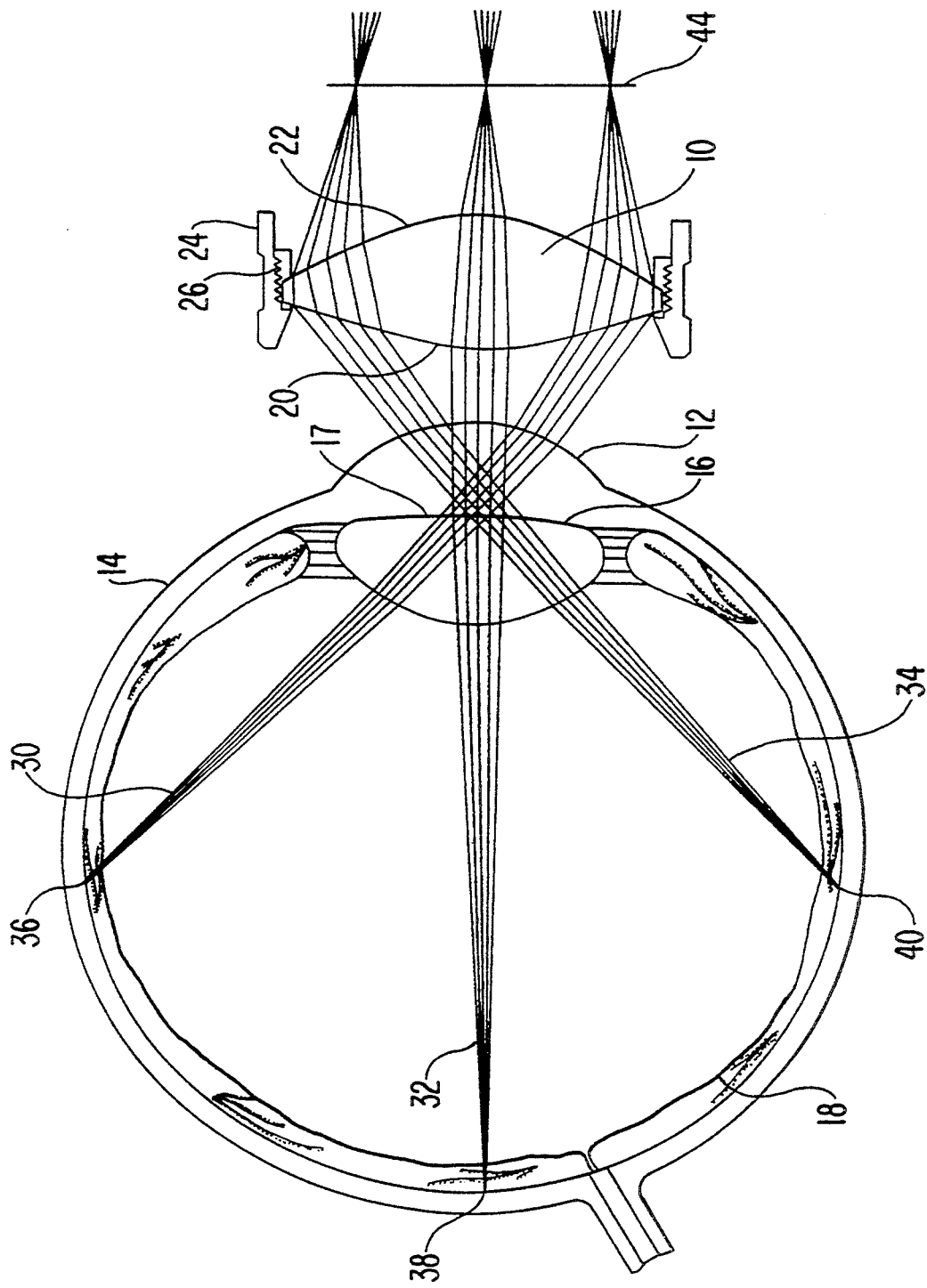
FIG. 1 is a schematic sectional view of a single element, non-contact lens of the present invention shown positioned in relation to a patient's eye.

Referring to FIG. 1, there is shown a single element aspheric, indirect ophthalmoscopy lens 10 constructed in accordance with the present invention and positioned anterior of a cornea 12 of a patient's eye 14 which includes a crystalline lens 16, a pupil 17 and a retina 18. Indirect ophthalmoscopy lens 10 includes a posterior surface 20 and an anterior surface 22 and may be held in a retaining fixture 24 in a conventional manner with a threaded retaining insert 26. Other types of fixtures may be used to secure lens 10. For example, when used with an operating microscope (not shown), lens 10 may be fixed in a known microscope adapter assembly (also not shown).

Indirect ophthalmoscopy lens 10 is used in the usual manner to form a real, aerial image of the retina when placed an appropriate distance from cornea 12. Thus, as illustrated, bundles of light rays 30, 32 and 34 originating at and diverging from points 36, 38 and 40, respectively, on retina 18, pass through crystalline lens 16, exit the eye through pupil 17 and cornea 12. The light ray bundles then pass through lens 10 which focuses the light rays to form a real, aerial image 44. However, as contrasted with known prior art indirect ophthalmoscopy lenses, the image produced by the lens constructed according to the invention as described below, while in actuality being substantially planar, if not slightly over corrected, will appear to the observer to have a three dimensional concave curvature, giving a sense of the curvature of the actual retina due to the specific distortion introduced into the image as hereinafter described.

Each surface of lens 10 is characterized by the following polynomial formula:

$$Y = (2rx + (e^2 - 1)x^2)^{\frac{1}{2}} + Ax^F + Bx^G + Cx^H$$

where Y is the semi-diameter value; r is the apical radius of curvature; e is the apical eccentricity; x is the distance from the apex of the surface along its axis of revolution; A, B and C are constant coefficients; and F, G and H are constant exponents.

For both the posterior and anterior surfaces of the lens, r can range from about 0.003 m to about 0.221 m; e from about 0 to about 6.0; A, B, and C from about −80 to about +160; and F, G and H from about 0.5 to about 3.0. Thickness of lens 10 may range from about 0.001 m to about 0.020 m while diameter may range from about 0.005 m to about 0.070 m. Lens 10 can be made from any suitable optical material such as glass or plastic, including PMMA or CR-39 (allyl diglycol carbonate). Additionally, the index of refraction of the material selected may range from about 1.4 to about 2.1, covering the range of conventionally available clear optical materials.

In a preferred embodiment of the invention, one of the two lens surfaces, preferably the flatter of the two, may be defined simply as a conic, with the higher order terms of the equation omitted or set to zero, while the opposing surface will have active coefficients of substantial magnitude to achieve the stated optical characteristics of the present invention. In a specific example of this preferred embodiment, applicant made a lens wherein lens surface 20 was designed as a conoid with r=0.01589 m and e=3.0; and lens surface 22 was designed according to the following polynomial values: r=0.00935 m; e=2.0; A=1.1; B=−45.66; C=35.0; F=1.2; G=1.8; H=2.4. The lens was designed with a diameter of 0.019 m, a center thickness of 0.00535 m and the glass material had an index of refraction of 1.883.

Figure 2:
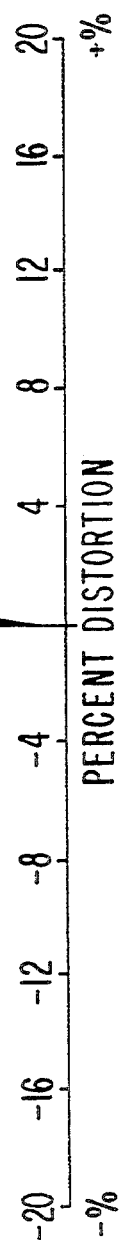
FIG. 2 is a graph showing distortion curves for images produced by the lens systems of FIGS. 1 and 3, respectively.

Turning now to FIG. 2, there is shown on the right-hand side of the graph a distortion curve of the single element non-contact lens of FIG. 1 constructed according to the above formula and polynomial values. The horizontal axis indicates percentage of distortion, which corresponds to relative magnification as previously discussed. Thus, an increasing percentage of distortion indicates an increasing magnification and a decreasing percentage of distortion indicates a decreasing magnification. The vertical axis represents the normalized field of the lens in air.

Generally speaking, indirect ophthalmoscopy lenses corrected for field curvature and astigmatism exhibit insufficient correction of distortion and as such, the aerial image produced may appear flat, as opposed to having a curved appearance corresponding to the curvature of the retina itself. A distortion plot of such a lens will show only negative distortion or insufficient distortion correction. If fully corrected for distortion, the indirect ophthalmoscopy lens exhibits poor field characteristics and excess magnification in the periphery of the image. The distortion plot of FIG. 2 represents not only a desirable compromise of distortion, defining a lens generally well corrected, if not slightly over corrected for field curvature, but additionally one that presents a three dimensional concave appearance that imparts to the observer a sense of the curvature of the actual retinal. Progressively increasing magnification peripheralward in the central region of the aerial image initially provides the sense of the visualized retina approaching the observer. Proceeding toward the periphery of the aerial image, magnification shifts direction, reducing image size and lateral magnification, thus providing a visual sense that an equatorial region of the retina is being approached. It is this unique character of continuously and progressively increasing, then decreasing magnification that promotes the visual sense of the three dimensional concave curvature of the retina according to the present invention. Furthermore, the reduced field of view normally resulting from excess peripheral magnification has been avoided by designing the indirect ophthalmoscopy lens according to the distortion characteristics shown.

Table I below lists in the first two columns the x values and corresponding Y values calculated at 0.0005 m increments (i.e. increments of the semi-diameter of the lens) using the foregoing polynomial formula with the polynomial values listed above for the lens of FIG. 1. The third column is the instantaneous eccentricity calculated at the corresponding x and Y points shown in the first two columns. As can be seen, the eccentricity progressively and continuously decreases from the center of the lens toward the periphery, attesting to the aspheric, non-conoidal shape of the lens according to the invention.

TABLE I

| Y | X | ECC |
| --- | --- | --- |
| .000500000 | .000013262 | 2.932212 |
| .001000000 | .000052280 | 2.559429 |
| .001500000 | .000115470 | 2.363625 |
| .002000000 | .000201007 | 2.227660 |
| .002500000 | .000307063 | 2.119918 |
| .003000000 | .000431951 | 2.027539 |
| .003500000 | .000574190 | 1.944101 |
| .004000000 | .000732534 | 1.865957 |
| .004500000 | .000905972 | 1.790843 |
| .005000000 | .001093717 | 1.717243 |
| .005500000 | .001295195 | 1.644070 |
| .006000000 | .001510026 | 1.570484 |
| .006500000 | .001738018 | 1.495785 |
| .007000000 | .001979154 | 1.419333 |
| .007500000 | .002233593 | 1.340484 |
| .008000000 | .002501674 | 1.258536 |
| .008500000 | .002783926 | 1.172652 |
| .009000000 | .003081088 | 1.081761 |
| .009500000 | .003394142 | .984386 |

Figure 3:
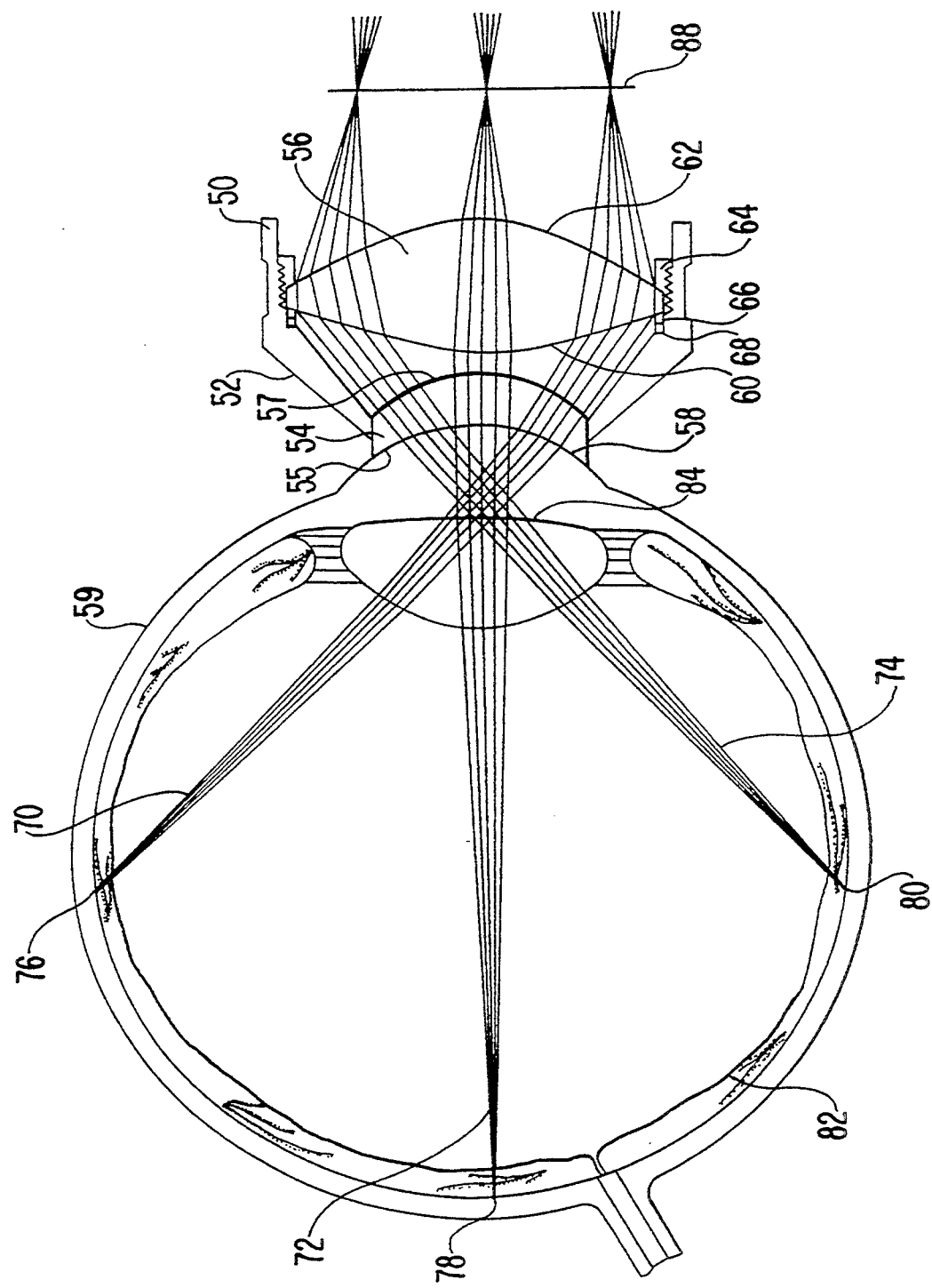
FIG. 3 is a schematic sectional view of a multiple element contact lens of the present invention shown positioned on a patient's eye.

Referring to FIG. 3, there is shown a multiple element, indirect ophthalmoscopy contact lens 50 including a cone shaped lens holder 52 securing and interconnecting a contact lens element 54 and an anterior lens element 56. Contact lens element 54 is mounted in the small end of cone shaped lens holder 52 and extends outwardly therefrom to enable contacting with a cornea 58 of a patient's eye 59. Contact lens element 54 may be secured in place with an optical glue, by means of interlocking threads or by other conventional means. Anterior lens element 56 is mounted slightly inwardly of the larger diameter end of cone shaped lens holder 52 to protect its outer (anterior) lens surface. Anterior lens element 56 is maintained in a fixed position by a conventional threaded retaining ring 64 against a compressible O-ring 66, which itself abuts against a shoulder 68 of cone shaped holder 52. Lens holder 52 allows manipulation of the ophthalmoscopy lens 50 when operatively disposed with contact lens element 54 in place against the eye 58 of a patient.

Both contact lens element 54 and anterior element 56 may be made of homogenous transparent optical material, such as glass or plastic, the index of refraction of the material ranging from about 1.4 to about 2.1. Contact lens element 54 has posterior and anterior surfaces 55 and 57, respectively, and anterior lens element 56 has posterior and anterior surfaces 60 and 62, respectively, each of which surfaces can be characterized by the foregoing polynomial formula. One or both surfaces of anterior lens 56 or of a plurality of lens elements anterior to the contact lens element may incorporate the aspheric, non-conoidal surface contributing to the variable magnification characteristics of the present invention. For simplicity in design and ease of manufacturing, it is preferable to limit this aspheric, non-conoidal shape to the anterior or steeper lens surface of the most anterior lens element (i.e. surface 62 in FIG. 3).

Each of the lens surfaces of the contact lens element may have the profile of a conoid, meaning that the higher order terms of the polynomial formula are set to zero. Preferably, for the posterior contact lens surface 55, r can range from about 0.007 m to about 0.0084 m, and e from about 0.0 to about 0.9. For the anterior contact lens surface r can range from about 0.004 m to about 0.100 m and e from about 0.0 to about 3.0. Thickness of the contact lens may range from about 0.0005 m to about 0.015 m while the diameter of its useable optical portion may range from about 0.004 m to about 0.020 m. For both the posterior and anterior surfaces 60, 62 of anterior lens 56, r can range from about 0.003 m to about 0.221 m; e from about 0 to about 6.0; A, B, and C from about $-80$ to about $+160$; and F, G and H from about 0.5 to about 3.0. Thickness of the anterior lens 56 may range from about 0.001 m to about 0.020 m while diameter may range from about 0.005 m to about 0.050 m. Spacing between contact lens element 54 and anterior lens element 56 may range from about 0.00005 m to 0.025 m.

The optical material may be treated to include light filtering properties for absorbing specific wavelengths of light. It is preferred that contact lens element 54 be made of Polymethylmethacrylate and anterior element 56 of optical glass, such as Schott LAKN16 with an index refraction of 1.734. Both surfaces of anterior element 56 and the anterior surface of contact lens element 54 may be coated with an anti-reflective coating to minimize reflections and increase light transmission.

As shown in FIG. 3, light ray bundles 70, 72 and 74 originating at and diverging from points 76, 78 and 80, respectively, of retina 82, exit eye 59 through pupil 84 and cornea 58 and are refracted by contact element 54 towards anterior lens element 56 which focuses the converging light ray bundles at aerial image 88.

A contact indirect ophthalmoscopy lens constructed according to the invention may be used with the slit lamp biomicroscope, operating microscope or other instrument. Because a variety of lenses of different power are utilized with each instrument, a variety of lenses of different design, power and configuration may be utilized in combination with the principles of the present invention which employ variable magnification to produce the three dimensional effect of the retinal image. The lens of FIG. 3, as an example, may be constructed for use with an operating microscope in vitreoretinal surgery, and used with a suture down scleral ring (not shown).

In a specific example of a contact indirect ophthalmoscopy lens illustrated in FIG. 3, posterior and anterior surfaces 55, 57 of contact lens element 54 each have a conoidal shape, wherein for the posterior surface 55, $r=0.0077$ m and $e=0.425$; and for the anterior surface 57, $r=0.00695$ m and $e=0.425$. Contact lens element 54 is made of polymethylmethacrylate with an index of refraction of 1.491 and has a diameter of 0.0105 m and center thickness of 0.0024 m. Spacing between the contact lens element and the anterior lens element is 0.0005 m.

The posterior surface 60 of anterior lens 56 is also designed as a conoid with $r=0.01248$ m and $e=2.64$. The anterior surface 62 of anterior lens 56 is designed according to the above polynomial formula wherein $r=0.00805$ m; $e=1.43$; $A=1.1$; $B=-27.35$; $C=35$; $F=1.2$; $G=1.8$; and $H=2.4$. Anterior lens element 56 is produced from an optical quality glass with an index of refraction of 1.734, has a diameter of 0.01626 m and a center thickness of 0.006 m.

Referring again to FIG. 2, there is shown on the left-hand side of the graph a distortion curve for the foregoing example of the multi-element, contact, indirect ophthalmoscopy lens illustrated in FIG. 3. As with the distortion curve of the single, non-contact, indirect ophthalmoscopy lens illustrated on the right-hand side of FIG. 2, the distortion characteristics shown represent not only a desirable compromise of distortion, defining a lens generally well corrected, if not slightly over corrected for field curvature, but additionally one that represents a concave fundus appearance, thus imparting a sense of the actual curvature of the retina being imaged. Progressively increasing magnification peripheralward in the central region of the aerial image initially provides the sense of the visualized retina approaching the observer. Proceeding toward the periphery of the image, the distortion curve indicates that magnification shifts direction, reducing image size and lateral magnification, thus providing a visual sense that an equatorial region of the retina is being approached.

Preferably, the variable distortion according to the invention is positive in the central region by no more than about 10% and is negative in the peripheral region by no more than 15%. It is additionally preferable that the total distortion for any one lens system vary by no more than an absolute value of 15% over the extent of the real, aerial image.

Table II below lists in the first two columns the x values and corresponding Y values at 0.0005 m increments of the semi-diameter, describing the anterior lens surface 62 of anterior lens 56 of the multiple element indirect ophthalmoscopy lens according to the polynomial parameter values of the foregoing example. The third column shows the calculated instantaneous eccentricity values for the corresponding values of x and Y. As with the lens of FIG. 1, the anterior lens surface 62 of lens 56 demonstrates continuously and progressively decreasing eccentricity toward the periphery of the lens surface, attesting to the aspheric, non-conoidal shape of the lens surface.

TABLE II

| Y | X | ECC |
|---|---|---|
| .0005 | .0000154 | 2.513254 |
| .0010 | .0000608 | 2.143257 |
| .0015 | .0001345 | 1.952909 |
| .0020 | .0002349 | 1.824425 |
| .0025 | .0003602 | 1.725957 |
| .0030 | .0005088 | 1.644595 |
| .0035 | .0006795 | 1.573918 |
| .0040 | .0008710 | 1.510303 |
| .0045 | .0010826 | 1.451518 |
| .0050 | .0013134 | 1.396095 |
| .0055 | .0015630 | 1.343020 |
| .0060 | .0018310 | 1.291556 |
| .0065 | .0021174 | 1.241149 |
| .0070 | .0024223 | 1.191366 |
| .0075 | .0027460 | 1.141849 |
| .0080 | .0030888 | 1.092296 |
| .0085 | .0034517 | 1.042437 |
| .0090 | .0038354 | .992014 |
| .0095 | .0042413 | .940777 |

In summary, the present invention provides a variety of lens types in an improved indirect ophthalmoscopy lens system, producing a clear and focused aerial image of the fundus and vitreoretinal structures of the eye with unique optical properties aiding the practitioner in various diagnostic, treatment and surgical procedures where an appreciation of the curvature of the retinal image is desirable or required. Although preferred embodiments of the invention have been described, it is to be understood that various modifications would be obvious to those skilled in the art and are embodied within the present invention as defined by the appended claims.

What is claimed is:

1. In an ophthalmoscopy lens system for collecting light rays emanating from a patient's eye and focussing the collected light rays to produce a real aerial image of the fundus of the patient's eye, the improvement wherein said ophthalmoscopy lens system includes a plurality of lens surfaces which collectively produce a variable distortion over the extent of the aerial image so that the aerial image, as viewed by an observer from a position anterior of said ophthalmoscopy lens system, has an apparent three dimensional concave curvature.

2. The ophthalmoscopy lens system according to claim 1, wherein at least one of said plurality of lens surfaces has an aspheric, non-conoidal shape contributing to the variable distortion.

3. The ophthalmoscopy lens system according to claim 2, wherein said at least one surface has instantaneous eccentricity values which progressively and continuously decrease from a center point of said at least one surface to the periphery of said at least one surface.

4. The ophthalmoscopy lens system according to claim 1, wherein said ophthalmoscopy lens system comprises a single non-contact lens element having posterior and anterior surfaces and at least one of said posterior and anterior surfaces has an aspheric, non-conoidal profile contributing to the variable distortion.

5. The ophthalmoscopy lens system according to claim 4, wherein said anterior surface has the profile of the aspheric, non-conoid.

6. The ophthalmoscopy lens system according to claim 1, wherein the real, aerial image has a central region and a peripheral region surrounding said central region, and wherein the variable distortion continuously and progressively increases outwardly from a center point of the image in the central region and continuously and progressively decreases in an outward direction throughout the peripheral region.

7. The ophthalmoscopy lens system according to claim 6, wherein the distortion in the central region is positive by no more than about 10% and the distortion in the peripheral region is negative by no more than about 15%.

8. The ophthalmoscopy lens system according to claim 1, wherein said ophthalmoscopy lens system comprises a contact lens element having a concave posterior surface for placement on the cornea of a patient's eye and a convex anterior surface; and an anterior lens element spaced in the anterior direction from the contact lens element, with at least one of the surfaces of said contact lens element and said anterior lens element being shaped to contribute to said variable distortion; and a lens holder for securing and interconnecting said contact lens and anterior lens elements.

9. The ophthalmoscopy lens system according to claim 8, wherein said at least one surface comprises one of the surfaces of said anterior lens element.

10. The ophthalmoscopy lens system according to claim 9, wherein the anterior surface of said anterior lens element has the aspheric, non-conoidal profile for contributing to the variable distortion.

11. The ophthalmoscopy lens system according to claim 1, wherein the plurality of lens surfaces are shaped to provide correction of field curvature while simultaneously producing the variable distortion.

12. The ophthalmoscopy lens system according to claim 1, wherein the plurality of lens surfaces are shaped to provide an over-correction of field curvature while simultaneously producing the variable distortion.

13. The ophthalmoscopy lens system according to claim 1, wherein said lens system includes a biconvex aspheric lens in which each surface of said biconvex aspheric lens characterized by the following formula:

$$Y = (2rx + (e^2 - 1)x^2)^{\frac{1}{2}} + Ax^F + Bx^G + Cx^H;$$

where Y is the semi-diameter distance from the optical axis; x is the distance from the apex of the surface along its axis of revolution; r is the apical radius of curvature and has a range from about 0.003 m to about 0.221 m; e is the apical eccentricity and has a range from about 0 to about 6.0; A, B and C are constant coefficients and have a range from about −80 to about 160; and F, G and H are constant exponents and have a range from about 0.5 to about 3.0; and wherein values for r, e, A, B, C, F, G and H for each surface are selected within said ranges to produce the variable distortion over the extent of the aerial image.

14. The ophthalmoscopy lens system according to claim 13, wherein said biconvex lens has posterior and anterior surfaces and said posterior surface has a conoidal profile and said anterior surface has an aspheric, non-conoidal profile.

15. The ophthalmoscopy lens system according to claim 14, wherein for said posterior surface: $r = 0.01589$ m, $e = 3.0$ and the constant coefficients A, B, and C are zero; and for said anterior surface: $r = 0.00935$ m; $e = 2.0$; $A = 1.1$; $B = -45.66$; $C = 35.0$; $F = 1.2$; $G = 1.8$; $H = 2.4$.

16. The ophthalmoscopy lens system according to claim 15, wherein said biconvex lens has a center thickness of about 0.00535 m.

17. The ophthalmoscopy lens system according to claim 14, and further comprising a contact lens and a lens holder mounting the contact lens and the biconvex lens in a fixed, spaced apart relationship, said contact lens having a posterior surface with a curvature adapted to be placed on the cornea of a patient's eye.

18. The ophthalmoscopy lens system according to claim 17, wherein for said posterior surface: $r=0.01248$ m, $e=2.64$ and the coefficients A, B and C are zero; and for said anterior surface: $r=0.00805$ m; $e=1.43$; $A=1.1$; $B=-27.35$; $C=35$; $F=1.2$; $G=1.8$; and $H=2.4$.

19. The ophthalmoscopy lens system according to claim 18, wherein said biconvex lens has and a center thickness of about 0.006 m.

20. The ophthalmoscopy lens system according to claim 13, and further comprising a contact lens and a lens holder mounting the contact lens and the biconvex lens in a fixed, spaced apart relationship, said contact lens having a posterior surface with a curvature adapted to be placed on the cornea of a patient's eye.

21. The ophthalmoscopy lens system according to claim 6, wherein the variable distortion varies by no more than 15% over the extent of the real, aerial image.

* * * * *